United States Patent [19]

Poling

[11] Patent Number: 5,092,852
[45] Date of Patent: Mar. 3, 1992

[54] SAFETY SYRINGE FOR SINGLE USE

[76] Inventor: Edward Poling, c/o Hung Hsing Patent Service Center P.O. Box 55-1670, Taipei, Taiwan

[21] Appl. No.: 655,745

[22] Filed: Feb. 15, 1991

[51] Int. Cl.⁵ .............................................. A61M 5/32
[52] U.S. Cl. .................... 604/192; 604/198; 604/263
[58] Field of Search ............... 604/192, 263, 110, 187, 604/198

[56] References Cited

U.S. PATENT DOCUMENTS

| | | | |
|---|---|---|---|
| 4,911,693 | 3/1990 | Paris | 604/192 |
| 4,927,416 | 5/1990 | Tomkiel | 604/198 |
| 5,013,301 | 5/1991 | Marotta, Jr. et al. | 604/198 X |

Primary Examiner—John D. Yasko

[57] ABSTRACT

A safety syringe includes a protective cap resiliently held on a needle of the syringe for preventing an unexpected injury to someone stuck by the needle, a locking tab detachably clamped on a needle holder of the needle, and at least a protrusion formed on the needle holder operatively engageable with a protrusion groove formed in a needle sleeve, whereby upon a removal of the locking tab from the needle holder and upon an inward depression of the needle holder and the needle into the needle sleeve to engage the protrusion on the needle holder with the groove formed in the sleeve, the needle will be permanently locked into the needle sleeve for a safer disposal of the needle with the sleeve.

11 Claims, 4 Drawing Sheets

SAFETY SYRINGE FOR SINGLE USE

BACKGROUND OF THE INVENTION

Eric C. Strauss disclosed an automatic protracting and locking hypodermic needle guard in his U.S. Pat. No. 4,664,654 comprising a sliding member 16 and a stationary member 28. Even the protrusions 24 can be engaged with the bevel shaped indention 37 to lock the needle tube 42, 41 within the sliding member 16 for its disposal. However, if the two protrusions 24 are accidentally compressed to disengage from the intention 37, the spring 30 will urge the needle 41 outwardly to cause injury or contamination to a nurse, a patient or anyone else.

Edward Klein disclosed a disposable safety medical syringe in his U.S. Pat. No. 4,955,868 by providing a shield wall 4 for protecting the hypodermic needle 1 within the wall 4. However, the shield wall 4 is resiliently urged outwardly by the spring 2, which will be easily compressed to retract the wall 4 inwardly to protrude the needle tip outwardly to still possibly cause injury or contamination accident. Besides, the shield wall 4 has a diameter larger than a diameter of the syringe wall 11 and the wall 4 has its front end portion provided with the shield opening 6 always urged by the spring 2 so that a puncture of the needle 1 will always be obstructed by the shield wall 4, thereby influencing a precise puncture on a patient skin for his or her medical treatment.

As shown in FIG. 6, a conventional syringe 1 includes a needle means 2 having a needle holder 22 secured with an adapter 11 of the syringe 1 and a needle 21 stored in a needle sleeve 5 having a central hole 52 formed in the sleeve 51. The needle 21 after being used can be easily withdrawn to cause contamination or injury to the others.

The present inventor has found the drawbacks of the conventional syringes, and invented the present safety syringe with single use.

SUMMARY OF THE INVENTION

The object of the present invention is to provide a safety syringe including a protective cap resiliently held on a needle of the syringe for preventing an unexpected injury to someone stuck by the needle, a lock means detachably clamped on a needle holder of the needle, and at least a protrusion formed on the needle holder operatively engageable with a protrusion groove formed in a needle sleeve, whereby upon a removal of the lock means from the needle holder and upon an inward depression of the needle holder and the needle into the needle sleeve to engage the protrusion on the needle holder with the groove in the sleeve, the needle will be permanently locked into the needle sleeve for ensuring a safe disposal of the needle with the needle sleeve to prevent their re-use.

DETAILED DESCRIPTION

Figures 1, 1A:
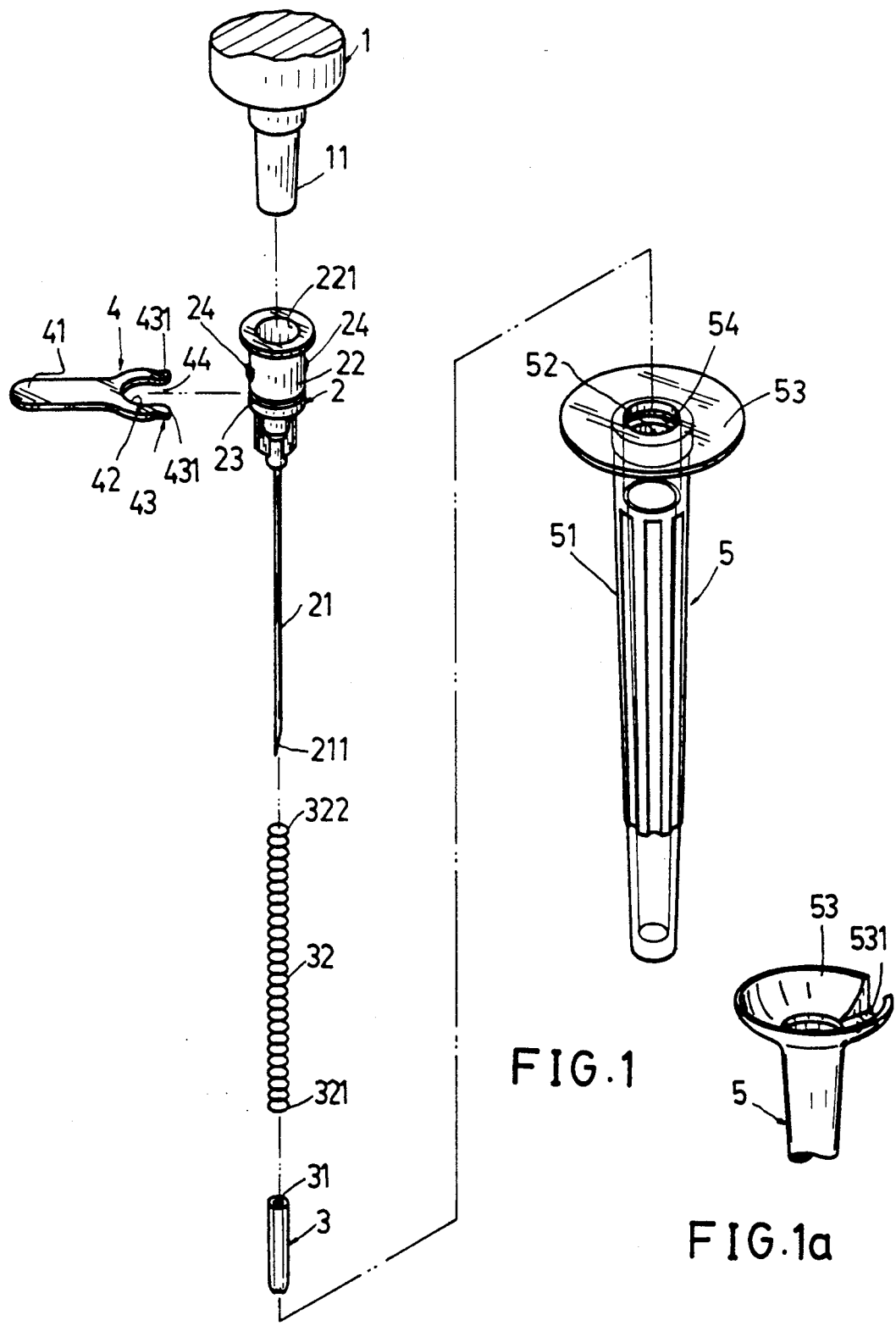
FIG. 1 is an exploded view showing all elements in construction of the present invention.
FIG. 1a shows another preferred embodiment of this invention.

As shown in FIGS. 1-5, the present invention comprises: a syringe 1, a needle means 2, a protective cap 3, a locking means 4, and a needle sleeve 5.

The syringe 1 may be a conventional syringe containing an injection liquid container and a plunger reciprocatively held in the liquid container (not shown) and includes an adapter 11 generally cylindrical shaped and formed on a lower portion of the syringe 1.

The needle means 2 includes: a hollow needle 21 having a tip 211 formed on a lowest end of the needle 21, a needle holder 22 secured with the needle 21 having a central hole 221 formed in the holder 22 engageable with the adapter 11 of the syringe 1 and fluidically communicated with the syringe 1 and the hollow needle 21, an annular groove 23 circumferentially formed in the needle holder 22, and at least a protrusion 24 formed on the holder 22. The groove 23 is positioned under the protrusion 24.

The protrusion 24 may be formed as a ratchet protrusion or an annular extension formed on a cylindrical or outer surface of the needle holder 22. The number of protrusions 24 of this invention is not limited and may be two protrusions 24 as shown in FIG. 1.

Figure 2:
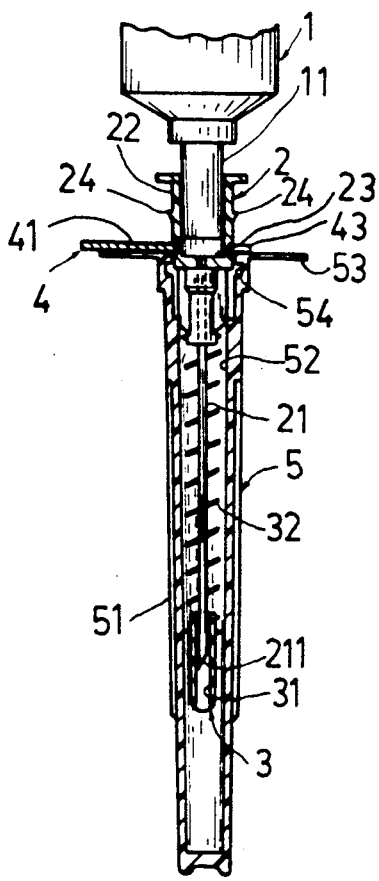
FIG. 2 is a sectional drawing of the present invention.
Figure 3:
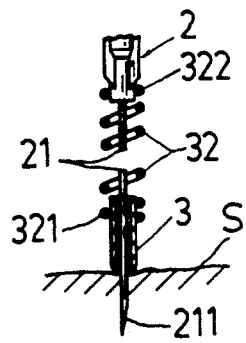
FIG. 3 is an illustration showing a puncture by the needle of the present invention.

The protective cap 3 may be made of transparent or translucent plastic materials for a clear vision of a needle tip 211 held through a needle hole 31 formed in the cap 3 as shown in FIGS. 2, 3. The cap 3 is resiliently secured to the needle holder 22 by a tensioning spring 32 having a lower spring end 321 secured with the cap 3 and an upper spring end 322 secured to the needle holder 22. The spring 32 should be firmly secured to the holder 22 and the cap 3 to prevent releasing from this invention for ensuring safety.

The locking means 4 includes: a handle 41, an U-shaped retainer 42 secured with the handle 41 and engageable with the annular groove 23 formed in the needle holder 22, and a spring clip 43 having two clamping portions 431 protruding outwardly from the U-shaped retainer 42 to define an aperture 44 therebetween with the aperture 44 being smaller in width than a diameter or width of the groove 23 for ensuring a firm stable normal engagement of the retainer 42 of the locking means 4 with the groove 23 of the needle means 2.

The shape of a cross section of the syringe adapter 11, the needle holder 22 and the sleeve 5 is not limited in this invention, but is preferably generally cylindrical shaped.

The locking means 4 may be made of metal such as an aluminum tab or plastic materials which are not limited in this invention.

The needle sleeve 5 includes: a sleeve body 51 having a length larger than that of the needle 21 and generally cylindrical shaped, a central sleeve hole 52 formed in the sleeve body 51 engageable with the needle holder 22 for holding the needle 21 in the sleeve hole 52, a finger protector 53 generally formed with a shielding flange radially protruding from a top periphery of the sleeve body 51, and a protrusion groove 54 annularly formed in the sleeve body 51 at an upper portion of the sleeve hole 52 to be engageable with the protrusion 24 of the needle means 2. The hole 52 is large enough for storing the cap 3 in the sleeve 5.

When using the present invention for a hypodermic injection or puncture, the needle holder 22 of the needle means 2 is fixed to the adapter 11 of the syringe 1 as shown in FIG. 2 and then withdrawn from the sleeve 5 for proceeding a puncture as shown in FIG. 3, wherein the needle tip 211 is poked into a patient's skin S by protruding the needle tip 211 downwardly outwardly from the cap 3 which is retained on a skin surface as shown in FIG. 3. After finishing the puncture, the needle 21 is pulled upwardly from the skin S and the tensioning spring 32 will urge the cap 3 outwardly to shield the tip 211 to prevent an unexpected sticking or injury or contamination to the others.

Before removing the locking means 4 from the needle means 2 (means 4 normally positioned between protrusion 24 and protector 53), the depression of said needle means 2 into the sleeve 5 will move the locking means 4 to be retarded by the finger protector 53 to prevent a permenent locking of the needle 21 in the sleeve 5 before using the needle 21.

Figure 4:
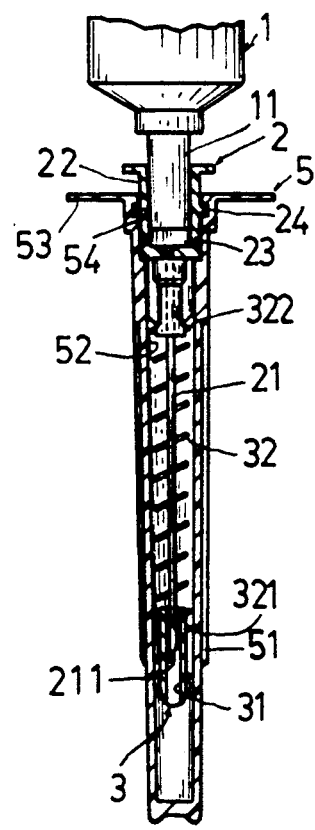
FIG. 4 is a sectional drawing of the present invention when pressing and engaging the needle into the needle sleeve.
Figure 5:
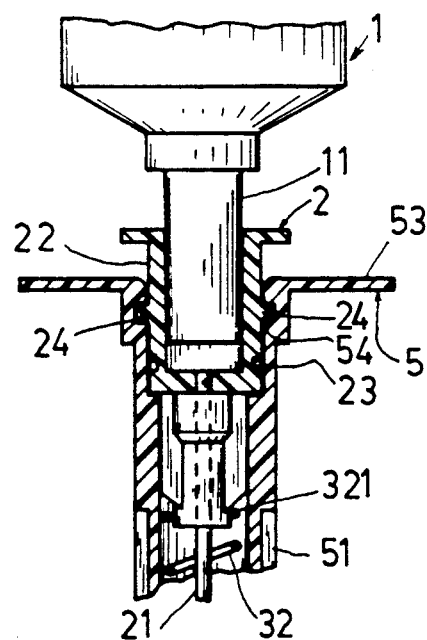
FIG. 5 is an enlarged illustration of FIG. 4 in accordance with the present invention.
Figure 6:
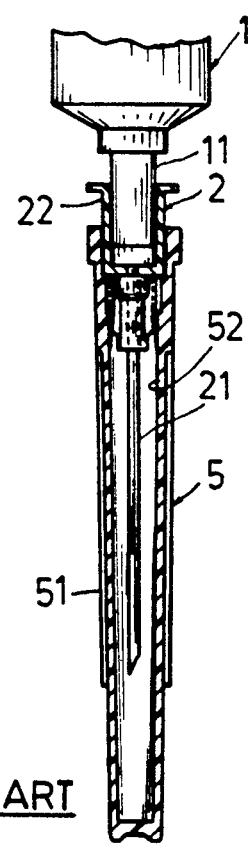
FIG. 6 shows a prior art of a conventional syringe.

After the injection treatment, the used needle 21 can be stored in the sleeve 5 by removing the locking means 4 from the groove 23 and by depressing the needle means 2 inwardly in order to engage the protrusions 24 with the annular groove 54 formed in the sleeve 5. Since the protrusion 24 may be made of ratchet shape as shown in FIGS. 5, 4 and once the protrusions 24 of the needle holder 22 are engaged with the groove 54 in the sleeve 5, the needle 21 will no longer be pulled outwardly from the sleeve 5 to ensure a permanent "locking" of the needle 21 in the sleeve 5 which can serve for a single use and can be disposed without causing contamination or injury to anyone. The finger protector 53 also protects a user's fingers when inserting the needle 21 into the sleeve 5.

Accordingly, this invention provides an absolute safe instrument of a syringe and a needle, to be superior to any conventional syringe.

As shown in FIG. 1a, the finger protector 53 may be formed as a cone shape tapered downwardly for an easier insertion of the needle 21 into the sleeve 5 when disposed. A flat path 531 is recessed in the protector flange 53 adapted for the insertion of the locking means 4 to be engaged with the groove 23 of the needle holder 22.

Figure 1B:
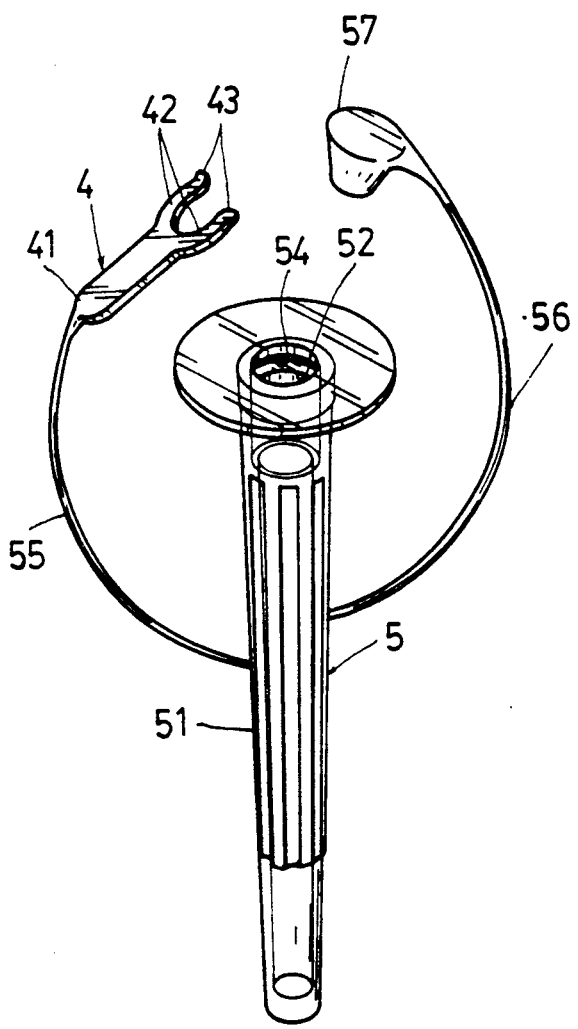

As shown in FIG. 1b, the sleeve 5 may be integrally formed with two straps 55, 56 for respectively connecting the locking means 4 and connecting a plug 57 for sealing the hole 221 after finishing the injection and inserting the needle means 2 into sleeve 5.

I claim:

1. A safety syringe comprising:
    a syringe having an adapter formed thereon;
    a needle means including a needle holder securable to the adapter of the syringe, an annular groove circumferentially formed in an outer surface of the needle holder, at least a protrusion formed on the needle holder, and a hollow needle secured to the needle holder having a tip formed on a lowest end of said needle;
    a protective cap resiliently secured to said needle holder for normally shielding the tip of the needle;
    a locking means engageably secured on said annular groove in said needle holder normally preventing a downward locking of said needle means in a needle sleeve; and
    the needle sleeve including a sleeve body having a central sleeve hole formed in the sleeve body engageable with said needle holder for storing said needle in said sleeve hole, and a protrusion groove annularly formed in said sleeve body operatively engageable with said protrusion of said needle means, whereby upon a removal of said locking means from said needle means and upon a depression of said needle means into said needle sleeve to engage said protrusion on said needle means with said protrusion groove in said needle sleeve, said needle with said needle means will be permanently locked in said sleeve for a safe disposal thereof.

2. A safety syringe according to claim 1, wherein said protrusion of said needle means is formed with a ratchet extension on said needle holder.

3. A safety syringe according to claim 1, wherein said protective cap includes a central needle hole formed therein for passing said needle therethrough, and a tensioning spring having a lower spring end secured with said cap and an upper spring end secured to said needle holder, said cap normally shielding said tip of said needle as urged by said spring.

4. A safety syringe according to claim 1, wherein said locking means includes: a handle, an U-shaped retainer secured with said handle engageable with said annular groove formed in said needle holder, and a spring clip secured to said retainer for clamping said locking means on said annular groove of said needle means.

5. A safety syringe according to claim 4, wherein said spring clip of said locking means includes two clamping portions protruding outwardly from said U-shaped retainer defining an aperture between the two clamping portions, said aperture having a width less than a diameter of said annular groove in said needle holder having a cross section generally cylindrical shaped.

6. A safety syringe according to claim 3, wherein said protective cap is made of transparent plastic materials.

7. A safety syringe according to claim 1, wherein said needle sleeve includes a finger protector generally formed as a shielding flange protruding radially outwardly from a top periphery of said sleeve body of said needle sleeve.

8. A safety syringe according to claim 4, wherein said annular groove of said needle holder engaged with said locking means is positioned under said protrusion of said needle holder, said locking means after being engaged with said annular groove in said needle holder normally retained above said finger protector of said sleeve to prevent a downward locking of said needle into said sleeve before using said needle.

9. A safety syringe according to claim 7, wherein said finger protector is formed with a cone shape tapered downwardly towards said sleeve adapted for smoothly receiving the tip of said needle.

10. A safety syringe according to claim 9, wherein said finger protector formed as a cone shape includes a flat path recessed in said protector for an insertion of said locking means to be engaged with the annular groove formed in said needle holder.

11. A safety syringe according to claim 1, wherein said needle sleeve is integrally formed with a first strap secured with said locking means and formed with a second strap secured with a plug sealable in a central hole formed in said needle holder.

* * * * *